US006783766B2

(12) United States Patent
Pate et al.

(10) Patent No.: US 6,783,766 B2
(45) Date of Patent: Aug. 31, 2004

(54) PROCESS FOR PREPARING A COSMETIC FORMULATION

(75) Inventors: James E. Pate, Sandford, MI (US); Dale C. Schmidt, Midland, MI (US); David L. Malotky, Midland, MI (US); Anthony S. Drager, Midland, MI (US); Christian Piechocki, Marienthal (FR)

(73) Assignee: Dow Global Technologies Inc., Midland, MI (US)

( * ) Notice: Subject to any disclaimer, the term of this patent is extended or adjusted under 35 U.S.C. 154(b) by 85 days.

(21) Appl. No.: 10/091,880

(22) Filed: Mar. 6, 2002

(65) Prior Publication Data

US 2003/0170193 A1 Sep. 11, 2003

(51) Int. Cl.[7] ............................. A61K 7/00; A61K 7/42
(52) U.S. Cl. ..................... 424/401; 424/59; 424/400; 514/937; 514/938; 514/939
(58) Field of Search .................... 424/400, 401, 424/59; 514/937, 938, 939

(56) References Cited

U.S. PATENT DOCUMENTS

| 4,018,426 A | 4/1977 | Mertz et al. ........... 259/7 |
| 4,446,127 A | 5/1984 | Bucheler et al. ........ 424/59 |
| 4,606,913 A | 8/1986 | Aronson et al. ........ 424/59 |
| 4,934,398 A | 6/1990 | Chirinos et al. ........ 137/13 |
| 4,980,167 A | 12/1990 | Harashima et al. ..... 424/401 |
| 5,266,321 A | 11/1993 | Shukuzaki et al. ..... 424/401 |
| 5,387,417 A | 2/1995 | Rentsch ............... 424/401 |
| 5,412,004 A | 5/1995 | Tachibana et al. ........ 524/27 |
| 5,437,867 A | 8/1995 | Vichroski et al. ....... 424/401 |
| 5,539,021 A | 7/1996 | Pate et al. ............ 523/335 |
| 5,585,109 A | 12/1996 | Hayward et al. ........ 424/450 |
| 5,597,574 A | 1/1997 | Narayanan et al. ...... 424/401 |
| 5,599,533 A | 2/1997 | Stepniewski et al. .... 424/78.02 |
| 5,654,362 A | 8/1997 | Schulz, Jr. et al. ..... 524/862 |
| 5,665,804 A | 9/1997 | Hill et al. ............. 524/268 |
| 5,688,842 A | 11/1997 | Pate, III et al. ........ 523/335 |
| 5,811,112 A * | 9/1998 | Chandar et al. ......... 424/401 |
| 5,833,973 A | 11/1998 | Dobkowski et al. ..... 424/18.08 |
| 5,849,314 A | 12/1998 | Dobkowski et al. ..... 424/401 |
| 5,871,761 A | 2/1999 | Kuwata et al. ......... 424/401 |
| 5,874,105 A | 2/1999 | Watkins et al. ......... 424/450 |
| 5,919,437 A | 7/1999 | Lee et al. ............. 424/68 |
| 5,919,468 A | 7/1999 | Bara .................. 424/401 |
| 5,928,660 A | 7/1999 | Kobayashi et al. ...... 424/401 |
| 5,948,855 A | 9/1999 | Lin et al. ............. 524/837 |
| 6,024,944 A | 2/2000 | Hansenne ............. 424/59 |
| 6,027,738 A | 2/2000 | Stepniewski et al. .... 424/401 |
| 6,039,935 A | 3/2000 | Mohammadi .......... 424/59 |
| 6,074,672 A | 6/2000 | Dobkowski et al. ..... 424/489 |
| 6,080,394 A | 6/2000 | Lin et al. ............. 242/78.03 |
| 6,083,900 A | 7/2000 | Auguste et al. ........ 512/2 |
| 6,103,250 A | 8/2000 | Brieva et al. ......... 424/401 |
| 6,126,948 A * | 10/2000 | Simonnet et al. ....... 424/101 |
| 6,177,071 B1 | 1/2001 | Lin et al. ............. 424/78.03 |
| 6,177,091 B1 | 1/2001 | Bara et al. ........... 424/401 |
| 6,221,927 B1 | 4/2001 | Lin et al. ............. 521/64 |
| 6,221,979 B1 | 4/2001 | Lin et al. ............. 525/477 |
| 6,228,348 B1 * | 5/2001 | Simon et al. .......... 424/59 |
| 6,235,292 B1 | 5/2001 | Bara et al. ........... 424/401 |
| 6,248,339 B1 | 6/2001 | Knitowski et al. ....... 424/401 |
| 6,406,684 B1 | 6/2002 | Fecht et al. .......... 424/65 |
| 2001/0022965 A1 | 9/2001 | Heger et al. .......... 424/59 |
| 2002/0143072 A1 | 10/2002 | Aust et al. ........... 516/98 |
| 2003/0026856 A1 | 2/2003 | Aust et al. ........... 424/725 |
| 2003/0175316 A1 | 9/2003 | Pate et al. ........... 424/401 |

FOREIGN PATENT DOCUMENTS

| EP | 0295886 | 1/1992 |
| EP | 054002 | 8/1992 |
| EP | 0242219 | 10/1992 |
| EP | 0732144 A1 | 9/1996 |
| EP | 0787758 A1 | 8/1997 |
| EP | 0829253 | 3/1998 |
| EP | 0869142 | 10/1998 |
| EP | 0917870 | 5/1999 |
| EP | 1020494 | 7/2000 |
| EP | 1057872 | 12/2000 |
| EP | 1069150 | 1/2001 |
| EP | 1163951 | 12/2001 |
| EP | 0848029 | 4/2002 |
| EP | 1048686 | 12/2002 |
| EP | 0934959 | 4/2003 |
| WO | WO 9421234 | 9/1994 |
| WO | WO 99/43297 | 9/1999 |
| WO | WO 01/54663 | 2/2001 |
| WO | WO 01/54663 | 8/2001 |
| WO | WO 0154663 | 8/2001 |
| WO | WO 0158238 | 8/2001 |
| WO | WO 01/70197 | 9/2001 |

(List continued on next page.)

OTHER PUBLICATIONS

Clarson, S J., *Siloxane Polymers*, PTR Prentice Hall, New Jersey, 1993, pp. 465–468, 567, 616–617.
Becher, Paul, *Emulsions Theory and Practice*, Oxford University Press, New York, 2001, pp. 83–85.
Starch, Michael, "New Developments in Silicone Elastomers for Skin Care," Dow Corning. Form No. 27–1060A, 2002, pp. 1–8.

*Primary Examiner*—Shelley A. Dodson

(57) ABSTRACT

The present invention is a process of preparing an advanced cosmetic product by combining a high internal phase ratio (HIPR) emollient-in-water emulsion with a partial cosmetic formulation that typically contains water, fragrance, a rheology modifier, or a pH adjuster, or a combination thereof. The present invention is also a composition comprising two particular subclasses of HIPR emollient-in-water emulsions, namely an HIPR silicone elastomer-in-water emulsion and an HIPR sunscreen-in-water emulsion. The use of an HIPR emulsion of a cosmetic emollient provides a simple and flexible method of formulating the cosmetic product, due in part to the long shelf-stability of the HIPR emulsion (>1 year), and the low quantity of water in the emulsion (typically less than 20% by volume based on the volume of emollient and water).

17 Claims, No Drawings

FOREIGN PATENT DOCUMENTS

| | | |
|---|---|---|
| WO | WO 0170270 | 9/2001 |
| WO | WO 1070197 | 9/2001 |
| WO | WO 0203916 | 1/2002 |
| WO | WO 0203925 | 1/2002 |
| WO | WO 0203929 | 1/2002 |
| WO | WO 02/03931 | 1/2002 |
| WO | WO 02/03932 | 1/2002 |
| WO | WO 02/03933 | 1/2002 |
| WO | WO 02/03934 | 1/2002 |
| WO | WO 02/03935 | 1/2002 |
| WO | WO 02/03950 | 1/2002 |
| WO | WO 02/03951 | 1/2002 |
| WO | WO 02/03952 | 1/2002 |
| WO | WO 0204004 | 1/2002 |

\* cited by examiner

PROCESS FOR PREPARING A COSMETIC FORMULATION

BACKGROUND OF THE INVENTION

The present invention relates to a process for preparing a cosmetic formulation. Historically, cosmetic formulations have been prepared by emulsifying an oil phase with an aqueous phase matrix using a batch process wherein the oil and water mixture is sheared in a large vessel. The oil phase typically includes a mixture of complex and varying oil-miscible ingredients and, consequently, batch-to-batch reproducibility of oil droplet size is often elusive. Moreover, processing time can be quite long and scale-up of the process from the benchtop to the manufacturing plant can be frustrating because tank-based processes often do not scale up in a linear fashion.

In WO 01/54663, Wilmott et al. discloses a possible solution to the problems associated with formulating personal care products by providing a substantially surfactant-free stable aqueous dispersion (that is, stable for at least two months), containing up to 70%, more preferably up to 50%, by weight of an oil phase, to which active ingredients can be added. This approach allows simple mixing of all ingredients, without the need for sub-phases or any special processing, to create a formulated cosmetic product. Nevertheless, there still remains an ever-increasing need to offer formulators more flexibility in controlling and fine tuning the properties of the final product, and to allow the formulators to use dispersions at their convenience.

SUMMARY OF THE INVENTION

The present invention addresses a need in the art by providing a process for preparing an advanced cosmetic product comprising the step of contacting a high internal phase ratio (HIPR) emollient-in-water emulsion with a partial cosmetic formulation to produce the advanced cosmetic product.

The process of the present invention reduces significantly the amount of water initially added to the formulated product, thereby providing a distinct advantage to the formulator for controlling the texture, sensation, consistency, shelf stability, and deliverability of active agents of the cosmetic product.

In a second aspect, the present invention is a composition comprising an HIPR silicone elastomer-in-water emulsion.

In a third aspect, the present invention is a composition comprising an HIPR sunscreen agent-in-water emulsion, wherein the sunscreen agent contains at least one chromophoric group absorbing in the ultraviolet range from 290 to 400 nm.

DETAILED DESCRIPTION OF THE INVENTION

In the process of the present invention, a high internal phase ratio (HIPR) emollient-in-water emulsion is contacted with a partial cosmetic formulation to produce an advanced cosmetic product. In general, HIPR emulsions are characterized by a disperse phase of polyhedral cells at a volume fraction of at least 74% (the most compact arrangement of spheres of equal radius) dispersed in a continuous phase that forms a thin film separating the cells.

As used herein, the word "emollient" refers to one or more water-immiscible substances used in cosmetic formulations; the term "water-immiscible substance" refers to a compound capable of forming an HIPR emulsion with water. Examples of emollients include i) mineral oil, petrolatum, polydecene, and isohexadecane; ii) fatty acids and alcohols having from 10 to 30 carbon atoms such as pelargonic, lauric, myristic, palmitic, steraric, isostearic, hydroxystearic, oleic, linoleic, ricinoleic, arachidic, behenic, and euricic acids and alcohols; iii) triglyceride esters such as castor oil, cocoa butter, safflower oil, sunflower oil, jojoba oil, cottonseed oil, corn oil, olive oil, cod liver oil, almond oil, avocado oil, palm oil, sesame oil, squalene, Kikui oil, and soybean oil; iv) acetoglyceride esters such as acetylated monoglycerides; v) ethoxylated glycerides such as ethoxylated glyceryl monostearate; vi) alkyl esters of fatty acids having 10 to 20 carbon atoms such as hexyl laurate, isohexyl laurate, isohexyl palmitate, isopropyl palmitate, decyl oleate, isodecyl oleate, hexadecyl stearate, decyl stearate, diisopropyl adipate, diisohexyl adipate, diisopropyl sebacate, laurly lactate, myristyl lactate, and cetyl lactate; vii) alkenyl esters of fatty acids having 10 to 20 carbon atoms such as oleyl myristate, oleyl stearate, and oleyl oleate; viii) fatty acid esters of ethoxylated fatty alcohols; ix) polhydric alcohol esters such as ethylene glycol mono and di-fatty acid esters, diethylene glycol mon- and di-fatty acid esters, and polyethylene glycol (200–6000) mon- and di-fatty acid esters; x) wax esters such as beeswax, spermaceti, myristyl myristate, and stearyl stearate; xi) silicone oils such as dimethicones and cyclomethicones.

Silicone elastomers constitute yet another class of emollients. These elastomers are advantageously prepared from the crosslinking reaction of a divinyl compound and a polysiloxane compound containing Si—H groups. Examples of commercially available silicone elastomers include General Electric Silicone 1229 (available from General Electric Company) and DC 9040 elastomer (available from Dow Corning Corporation, Midland, Mich.).

For the purposes of the present invention, sunscreen agents are also emollients. A sunscreen agent contains at least one chromophoric group that absorbs in the ultraviolet range of from 290 to 400 nm. Examples of chromophoric organic sunscreen agents include p-aminobenzoic acid as well as salts and esters thereof; o-aminobenzoic acid and o-aminobenzoates (including methyl, menthyl, phenyl, benzyl, phenylethyl, linalyl, terpinyl, and cyclohexenyl esters thereof); salicylic acid and salicylates (including octyl, amyl, phenyl, benzyl, menthyl, glyceryl, and dipropyleneglycol esters thereof); cinnamic acid and derivatives thereof (including menthyl and benzyl esters, alpha-phenyl cinnamonitrile, and butyl cinnamoyl pyruvate); dihydroxycinnamic acid and its derivatives; trihydroxycinnamic acid and its derivatives; diphenylbutadiene and stilbene; dibenzalacetone and benzalacetophenone; naphthosulfonates (such as sodium salts of 2-naphthol-3,6-disulfonic acid and 2-naphthnol-6,8-disulfonic acid); dihydroxynaphthoic acid and its salts; o- and p-hydroxydiphenyldisulfonates; coumarin and derivatives thereof (such as 7-hydroxy, 7-methyl, and 3-phenyl coumarin); diazoles; quinine salts; quinoline and derivatives thereof; hydroxy- or alkoxybenzophenones; uric and vilouric acids; tannic acid and derivatives thereof; hydroquinone; benzophenones (such as oxybenzone, sulisobenzone, dioxybenzone, benzoresorcinol, 2,2',4,4'-tetrahydroxybenzophenone, 2,2'-dihydroxy-4,4'-dimethoxybenzophenone, octabenzone, 4-isopropyldibenzoylmethane, butylmethoxydibenzoylmethane, etocrylene, and 4-isopropyl-dibenzoylmethane).

Examples of commercially available sunscreen agents are listed in the following table. CTFA refers to Cosmetics, Toiletries, and Fragrances Association.

| CTFA Name | Trade Name | Supplier |
|---|---|---|
| Benzophenone-3 | UVINUL M-40 | BASF Chemical Co. |
| Benzophenone-4 | UVINUL MS-40 | BASF Chemical Co. |
| Benzophenone-8 | SPECTRA-SORB UV-24 | American Cyanamid |
| DEA-Methoxycinnamate | BERNEL HYDRO | Bernel Chemical |
| Ethyl dihydroxypropyl PABA | AMERSCREEM P | Amerchol Corp. |
| Glyceryl PABA | NIPA G.M.P.A. | Nipa Labs. |
| Homosalate | KEMESTER HMS | Humko Chemical |
| Menthyl Anthranilate | SUNAROME UVA | Felton Worldwide |
| Octocrylene | UVINUL N-539 | BASF Chemical Co. |
| Octyl dimethyl PABA | AMERSCOL | Amerchol Corp. |
| Octyl methoxycinnamate | PARSOL MCX | Bernel Chemical |
| PABA | PABA | National Starch |
| 2-Phenylbenzimidazole-5-sulfonic acid | EUSOLEX 6300 | EM Industries |
| TEA salicylate | SUNAROME W | Felton Worldwide |
| 2-(4-Methylbenzildene)-camphor | EUSOLEX 6300 | EM Industries |
| Benzophenone-1 | UVINUL 400 | BASF Chemical Co. |
| Benzophenone-2 | UVINUL D-50 | BASF Chemical Co. |
| Benzophenone-6 | UVINUL D-49 | BASF Chemical Co. |
| Benzophenone-12 | UVINUL 408 | BASF Chemical Co. |
| 4-Isopropyl dibenzoyl methane | EUSOLEX 8020 | EM Industries |
| Etocrylene | UVINUL N-35 | BASF Chemical Co. |

The HIPR sunscreen-in-water emulsion advantageously includes a stabilizing amount of an additive to prevent Ostwald ripening, that is, to prevent diffusion of the sunscreen active disperse phase from small droplets of the disperse phase to larger ones. The additive is a highly water-insoluble material that 1) has a negligible diffusion coefficient in the continuous aqueous phase and 2) is compatible with the disperse phase (for example, an emollient-phase compatible polymer such a polyisobutene; a long chain paraffin such as hexadecane; or a silicone such as silicone oil or dimethicone.) Preferably the additive is used in an amount not greater 5 weight percent, more preferably not greater than 2 weight percent, based on the weight of the sunscreen agent and the additive.

The HIPR emollient-in-water emulsion is stabilized by a stabilizing amount of a surfactant, which can be internal (that is, where the emollient itself acts as a surface active agent) or external. The concentration of the surfactant is preferably not less than 1% by weight, more preferably not less than 3% by weight, and preferably not more than 20% by weight, more preferably not more than 10% by weight, based on the weight of the emollient phase. External surfactants include nonionic, anionic, or cationic, or combinations of nonionic and anionic or nonionic and cationic.

Examples of nonionic surfactants suitable for stabilizing the HIPR emulsion include polyethylene glycol fatty acid mono- and diesters (such as PEG-8 laurate, PEG-10 oleate, PEG-8 dioleate, and PEG-12 distearate), polyethylene glycol glycerol fatty acid esters (such as PEG-40 glyceryl laurate and PEG-20 glyceryl stearate), alcohol-oil transesterification products (such as PEG-35 castor oil, PEG-25 trioleate, and PEG-60 corn glycerides), polyglycerized fatty acids (such as polyglyceryl-2-oleate and polyglyceryl-10 trioleate), propylene glycol fatty acid esters (such as propylene glycol monolaurate), mono- and diglycerides (such as glyceryl monooleate and glyceryl laurate), sterol and sterol derivatives (such as cholesterol), sorbitan fatty acid esters and polyethylene glycol sorbitan fatty acid esters (such as sorbitan monolaurate and PEG-20 sorbitan monolaurate), polyethylene glycol alkyl ethers (such as PEG-3 oleyl ether and PEG-20 stearyl ether), sugar esters (such as sucrose monopalmitate and sucrose monolaurate), polyethylene glycol alkyl phenols (such as PEG-10–100 nonyl phenol, and PEG-15–100 octyl phenol ether), polyoxyethylene-polyoxypropylene block copolymers (such as poloxamer 108 and poloxamer 182), and lower alcohol fatty acid esters (such as ethyl oleatea and isopropyl myristate).

Examples of suitable ionic surfactants include fatty acid salts (such as sodium laurate and sodium lauryl scarcosinate), bile salts (such as sodium cholate and sodium taurocholate), phospholipids (such as egg/soy lecithin and hydroxylecithin), phosphoric acid esters (such as diethanolammonium polyoxyethylene-10 oleyl ether phosphate), carboxylates (such as ether carboxylates and citric acid esters of mono and diglycerides), acyl lactylates (such as lactylic esters of fatty acids, and propylene glycol aginate), sulfates and sulfonates (such as ethoxylated alkyl sulfates, alkyl benzene sulfones, and acyl taurates), and alkyl, aryl, and alkyl-aryl sulfonates and phosphates. Examples of suitable cationic surfactants include quaternary ammonium salts and hydrochloride salts of N-alkyl diamines and triamines.

The HIPR emulsion can be prepared by a variety of methods, including batch and continuous methods well known in the art. In a preferred continuous method (described generally by Pate et al. in U.S. Pat. No. 5,539,021, column 3, line 15 to column 6, line 27, which passage is incorporated herein by reference) a stream containing the continuous aqueous phase is flowed through a first conduit and merged continuously with a stream of the disperse emollient phase that is flowed through a second conduit. The streams are merged into a disperser in the presence of a stabilizing amount of surfactant. The surfactant can be added to either stream, or as a separate stream, but is preferably added to the stream containing the emollient phase. The rates of the streams are adjusted within the HIPR emulsion region (74% to about 99%) so that particle size and polydispersity of the emulsion are optimized for the particular application. Preferably, the rates of the streams are adjusted so as to produce an HIPR emulsion having an emollient phase-to-aqueous phase ratio of from about 80% to about 95% by volume. The volume-average mean particle size of the emollient phase of the HIPR emulsion is application dependent. Though volume-average mean particle sizes of less than 1 $\mu$m are routinely achievable, submicron particle sizes may not be desirable in all cases. Generally, the preferred volume-average mean particle size is not greater than 50 $\mu$m, more preferably not greater than 20 $\mu$m, more preferably not greater than 10 $\mu$m, and most preferably not greater than 2 $\mu$m. However, when the emollient is a silicone elastomer, the desired volume-average mean particle size is preferably not less than 2 $\mu$m, more preferably not less than 10 $\mu$m, and most preferably not less than 20 $\mu$m; and preferably not greater than 100 $\mu$m, and more preferably not greater than 60 $\mu$m.

If the preferred continuous method for preparing the HIPR emulsion is used, the emollient phase must be flowable through the conduit. If the emollient is sufficiently low in viscosity so as to be flowable at ambient temperature and without dilution of solvent, the HIPR emulsion is preferably prepared at ambient temperature and without the use of an ancillary solvent for the emollient. If, on the other hand, the emollient is not flowable through the conduit at ambient temperature, either because it is a solid or a highly viscous liquid at ambient temperature, the emollient can be rendered flowable by either heat or solvent addition. For example, where the emollient is a silicone elastomer, it is desirable to add a solvent for the elastomer in a sufficient amount so as to render the silicone elastomer flowable through the conduit. Preferred solvents for the silicone elastomer include cyclomethicones, dimethicones, or a low viscosity emollient.

Minor amounts, preferably not greater than 5%, more preferably not greater than 1%, and most preferably not greater than 0.5% by weight, of water-compatible substances, that is, substances which, by themselves are incapable of forming aqueous HIPR emulsions, can be added to the emollient prior to emulsification of the emollient. Examples of such water-compatible substances include rheology modifiers such as carbomers, acrylic copolymers, polyacrylamides, polysaccharides, natural gums, and clays; preservatives such as alkyl esters of p-hydroxybenzoic acid; humectants such as glycerol; and pH modifiers.

The HIPR emulsion used in the process of the present invention is combined with a partial cosmetic formulation to produce an advanced cosmetic product. As used herein, "partial cosmetic formulation" refers to one or more finishing ingredients, which, when combined with the HIPR emulsion, form an advanced, and preferably a finished, cosmetic product. The term "advanced cosmetic product" refers to either a finished cosmetic product or one that is closer to being a finished product than before the HIPR emulsion and partial cosmetic formulation were combined. Preferably, the advanced cosmetic product is a finished cosmetic product that is ready to be packaged for and sold to the consumer. In an extreme case, the HIPR emulsion may contain all of the ingredients of the finished product, and the partial cosmetic formulation is simply water. In this case, the HIPR emulsion represents a concentrate of the finished product, which is merely diluted with water to form the finished product.

Although it is possible to prepare an HIPR emulsion that includes the ingredients commonly found in a partial cosmetic formulation such as color, fragrance, rheology modifier, or pH adjuster, it may be desirable to exclude these ingredients from the HIPR emulsion. For example, color, fragrance, rheology, or pH may be more easily controlled when included in the partial cosmetic formulation and combined with an HIPR emulsion that contains predominantly the emulsified emollient. The HIPR emulsion and the partial cosmetic formulation can be combined concomitantly or in any order. Furthermore, more than one HIPR emulsion can be combined with the partial cosmetic formulation to form the advanced cosmetic product. For example, an HIPR emulsion of mineral oil and a separately prepared HIPR emulsion of petrolatum can be combined with a partial cosmetic formulation containing water, thickener, fragrance, and color to form a body lotion. Examples of finished cosmetic products include hand lotion, body lotion, body wash, conditioners, shampoos, and facial creams.

The process of the present invention provides a simple and flexible method of formulating the cosmetic product, due to the ease with which an HIPR emulsion with controlled particle size can be reproduced, to the long shelf-stability of the HIPR emulsion (>1 year), and to the low quantity of water in the emulsion (less than 26%, and preferably less than 20% by volume, based on the volume of emollient and water).

The following examples are for illustrative purposes only and are not intended to limit the scope of the invention. All percentages are by weight unless otherwise specified. Particle sizes of HIPR emulsions are measured using a Coulter LS 230 Laser Light Scattering Particle Sizer (Coulter Corp.).

EXAMPLE 1

Procedure for Preparing a Concentrated Silicone Elastomer Emulsion

An HIPR emulsion containing Dow Corning 9040 Silicone Elastomer Blend is prepared in the following manner. First, Dow Corning 345 fluid (19.5%) and TERGITOL™ 15-s-12 (a trademark of The Dow Chemical Company, 2.4%, secondary alcohol ethoxylate surfactant) are added to the Dow Corning 9040 Elastomer Blend (78.1%). The ingredients are mixed until uniform in a vessel with both sweep and helical agitation. This disperse phase is pumped by a Zenith gear pump at a rate of 30 g/min through ½-inch stainless steel tubing into a four-inch diameter Oakes rotor stator mixer spinning at 800 rpm. The disperse phase is merged at the mixer with a separate deionized water stream phase containing a DOWICIL™ 200 antimicrobial (a trademark of The Dow Chemical Company, 0.05% based on the weight of the water). This continuous water phase is pumped into the mixer through ¼-inch stainless steel tubing using an Alltech liquid chromatography pump at a rate of 5.7 g/min. The emollient phase is 82 weight %, based on the weight of all of the materials in the HIPR emulsion (65.6 weight % of the silicone elastomer and 16.4 weight percent of Dow Corning 345 fluid). The resultant HIPR emulsion has a volume-average mean particle size of 30 μm.

EXAMPLE 2

Procedure for Making a Concentrated Silicone Elastomer

An HIPR emulsion containing Dow Corning 9040 Elastomer is prepared in the following manner. First, Mirasil 500,000 centistoke silicone fluid (7%) is added to the Dow Corning 9040 Elastomer (93%) and heated to 70° C. The ingredients are then mixed until uniform with a bench top mixer at 70° C. This disperse phase is pumped by a Zenith gear pump at a rate of 22 g/min through ½-inch stainless steel tubing into a four-inch diameter Oakes rotor stator mixer spinning at 800 rpm. The rotor used had every other tooth removed on both sides. The disperse phase is merged at the mixer with a separate deionized water phase containing Rhodapex ES2 surfactant (28% active), 57% based on the total weight of the water phase). This continuous water phase is pumped into the mixer through ¼-inch stainless steel tubing using an Alltech liquid chromatography pump at a rate of 3.5 g/min. The resultant HIPR emulsion is 81 wt % Dow Corning 9040 elastomer based on the weight of all the materials in the emulsion, and has a volume-average mean particle size of 24 μm.

EXAMPLE 3

Procedure for Making a Concentrated Octyl Methoxy Cinnamate Emulsion

An HIPR emulsion containing Octyl Methoxy Cinnamate (Parsol MCX) is prepared in the following manner. First, Panalene L-14E hydrogenated polyisobutene (1.0% Hydrogenated Polyisobutene), Tween 60 surfactant (2.0% Polyoxyethylene 60 Sorbitan Monostearate surfactant) and Hamposyl M-30 surfactant (3% of the 30% aqueous solution, N-Methyl, N-(1-OxoTetradecyl) Glycine Sodium salt surfactant) are added to the Parsol MCX (94%). The ingredients are mixed until uniform in a vessel with both sweep and helical agitation. This oil phase is pumped by a Zenith gear pump at a rate of 34 g/min through ½-inch stainless steel tubing into a four-inch diameter Oakes rotor stator mixer spinning at 800 rpm. The phase is merged at the mixer with a separate deionized water stream phase containing DOWICIL 200 antimicrobial (0.05% based on the weight of the water). This continuous water phase is pumped into the mixer through ¼-inch stainless steel tubing using an Alltech liquid chromatography pump at a rate of 1.0 g/min. The resultant HIPR emulsion is 91% by weight Parsol MCX, based on the weight of all the ingredients in the emulsion. The emulsion has a volume-average mean particle size of 1.0 μm.

EXAMPLE 4
Procedure for Making a Finished Product Using an HIPR Triglyceride Emulsion The emollient phase for the HIPR Triglyceride Emulsion is prepared by melting TERGITOL 15-s-15 surfactant (2.5%) at 50° C. and adding it to triglyceride (96.4%), which has also been heated to 35° C. The material is then mixed for five minutes with a propeller mixer while maintaining temperature at 35° C. Next 0.5 wt % Hamposyl L-30 surfactant (30% active) and 0.21% DOWANOL™ EPh glycol ether (a trademark of The Dow Chemical Company), low phenol grade are mixed into the triglyceride with the propeller mixer. This disperse phase is pumped by a Zenith gear pump at a rate of 30 g/min through ½-inch stainless steel tubing into a four-inch diameter Oakes rotor stator mixer spinning at 500 rpm. The disperse phase is merged at the mixer with a separate deionized water stream phase containing a DOWANOL EPh glycol ether (2.4% based on the weight of the water). This continuous water phase is pumped into the mixer through a ¼-inch stainless steel tubing using an Alltech liquid chromatography pump at a rate of 1.5 g/min. The resultant HIPR emulsion has a volume-average mean particle size of 0.84 μm and is 92% triglyceride by weight based on the weight of all the materials in the emulsion.

This Concentrated Triglyceride Emulsion is then incorporated into a partial cosmetic formulation as follows. Deionized water (177.15 g), glycerin (15.0 g), trisodium EDTA (0.3 g), DOWICIL 200 antimicrobial (0.3 g) and concentrated triglyceride emulsion (30 g of 92% triglyceride) are placed in a 2 quart mixing bowl. The mixture is blended until uniform using a "flat beater" blade attachment on a KitchenAid mixer with a speed setting of 2. The mixer speed is then decreased to 1 and the 2% aqueous dispersion of Carbopol 980 carbomer (75 g) is added. Once the mixture is homogeneous, triethanol amine (1.5 g), Fragrance (0.75 g) and 2 drops of a 3% aqueous solution of food dye are added. The finished product is mixed until smooth. The finished product showed a volume-average mean particle size of 0.85 μm.

EXAMPLE 5
Procedure for Making a Finished Product Using an HIPR Petrolatum-in-Water Emulsion and an HIPR Jojoba Oil-in-Water Emulsion The oil phase for the concentrated petrolatum emulsion is created by melting 3.6% Brij 721 surfactant and 2.4% Brij 72 surfactant at 75° C. and adding these materials to 94% petrolatum, which has also been heated to 75° C. The material is then mixed for five minutes with a propeller mixer while maintaining temperature. This disperse phase is pumped by a Zenith gear pump at a rate of 30 g/min through ½-inch stainless steel tubing into a four-inch diameter Oakes rotor stator mixer spinning at 1800 rpm. The disperse phase is merged at the mixer with a separate deionized water phase containing DOWANOL EPh glycol ether (low phenol grade, 2.4% based on the total weight of the water phase) and Hamposyl L-30 surfactant (30% active, 21% based on total weight of the water phase). This continuous water phase is pumped into the mixer through a ¼-inch stainless steel tubing using an Alltech liquid chromatography pump at a rate of 2.0 g/min. The resultant HIPR emulsion has a volume-average mean particle size of 0.95 μm. This petrolatum HIPR emulsion is diluted in a centrifugal pump spinning at 500 rpm with a water stream identical to the first pumped at a rate of 2.5 g/min through ¼-inch stainless steel tubing using a Milroyal piston pump. This resultant HIPR emulsion is 80% by weight petrolatum based on the weight of all the materials in the emulsion.

The disperse phase for the HIPR Jojoba Oil emulsion is created by melting Brij 97 surfactant (4%) at 35° C. and adding it to jojoba oil (96%), which is also heated to 35° C. The material is then mixed for five minutes with a propeller mixer while maintaining temperature. This disperse phase is pumped by a Zenith gear pump at a rate of 30 g/min through ½-inch stainless steel tubing into a four-inch diameter Oakes stator rotor mixer spinning at 800 rpm. The disperse phase is merged at the mixer with a separate deionized water stream phase containing DOWICIL 200 antimicrobial (0.05% based on weight of the water phase). This continuous water phase is pumped into the mixer through a ¼-inch stainless steel tubing using an Alltech liquid chromatography pump at a rate of 1.2 g/min. The resultant HIPR emulsion has a volume-average mean particle size of 1.01 μM. This jojoba oil HIPR emulsion is diluted in a centrifugal pump spinning at 500 rpm with a water stream identical to the first pumped at a rate of 3.2 g/min through ¼-inch stainless steel tubing using a Milroyal piston pump. The resultant HIPR contains 83 wt % jojoba oil.

Both HIPR emulsions are then added to a partial cosmetic formulation as follows. Deionized water (156.15 g), glycerin (15.0 g), trisodium EDTA (0.3 g), DOWICIL 200 antimicrobial (0.3 g), HIPR (83%) jojoba emulsion (15 g) and HIPR (92%) petrolatum emulsion (36 g) are placed in a 400 mL plastic beaker. The mixture is blended until uniform using a 2-inch Cowles blade attachment on a Caframa® mixer with a speed of 300 RPM. The mixer speed is then decreased to 150 RPM and the 2% aqueous dispersion of Carbopol 980 carbomer (75 g) is added. Once the mixture is homogeneous, triethanol amine (1.5 g), Fragrance (0.75 g) and food dye (2 drops of a 3% aqueous solution) is added. The finished product is mixed until smooth. The finished product has a volume-average mean particle size of 1.02 μm.

What is claimed is:

1. A process for preparing a cosmetic product comprising the steps of (a) providing a high internal phase ratio emollient-in-water emulsion concentrate and (b) diluting the high internal phase ratio emollient-in-water emulsion concentrate with a partial cosmetic formulation, said partial cosmetic formulation comprising at least water; to produce the cosmetic product.

2. The process of claim 1 wherein the partial cosmetic formulation contains a fragrance, a rheology modifier, a preservative, a pH adjuster, or a combination thereof.

3. The process of claim 1 wherein the emollient includes a mineral oil, petrolatum, polydecene, isohexadecane, a fatty acid having 10 to 30 carbon atoms, a fatty alcohol having 10 to 30 carbon atoms, a triglyceride ester, an acetoglyceride ester, an ethoxylated glyceride, an alkyl ester of a fatty acid having 10 to 20 carbon atoms, an alkenyl ester of a fatty acid having 10 to 20 carbons atoms, a fatty acid ester of an ethoxylated fatty alcohol, a polyhydric alcohol ester, a wax ester, a silicone oil, a suncreen, or a combination thereof.

4. The process of claim 1 wherein the emollient includes a silicone elastomer.

5. The process of claim 1 wherein the high internal phase ratio emollient-in-water emulsion has volume-to-volume emollient-to-aqueous phase ratio of from about 80% to 95%.

6. The process of claim 1 wherein the emollient has a volume-average mean particle size of not greater than 10 μm.

7. The process of claim 1 wherein the emollient has a volume-average mean particle size of not greater than 2 μm.

8. The process of claim 1 wherein the high internal phase ratio emulsion contains a fragrance, a rheology modifier, a preservative, a pH adjuster, or a combination thereof.

9. The process of claim 1 wherein the cosmetic product is a finally formulated hand lotion, body lotion, body wash, conditioner, shampoo, or facial cream.

10. The process of claim 1 wherein the high internal phase ratio emulsion is prepared by the step of continuously merging into a disperser, in the presence of a stabilizing amount of surfactant, a disperse emollient phase stream and a continuous water phase at such flow rates as to yield an emollient-in-water high internal phase ratio emulsion.

11. A composition comprising a high internal phase ratio silicone elastomer-in-water emulsion.

12. The composition of claim 11 wherein the emulsion contains a solvent for the silicone elastomer.

13. The composition of claim 12 wherein the solvent for the silicone elastomer is a cyclomethiconeh a dimethicone or a combination thereof.

14. The composition of claim 11 wherein the emulsion has a volume-average mean particle size of not less than 20 μm and not greater than 100 μm.

15. The composition of claim 11 wherein the emulsion contains a fragrance, a rheology modifier, a preservative, or a pH adjuster, or a combination thereof.

16. A composition comprising a high internal phase ratio sunscreen agent-in-water emulsion, wherein the sunscreen agent contains at least one chromophoric group absorbing in the ultraviolet range from 290 to 400 nm.

17. The composition of claim 16 wherein the high internal phase ratio emulsion further includes a stabilizing amount of an additive to prevent Ostwald ripening.

* * * * *